United States Patent [19]

van der Kerk et al.

[11] 4,039,655

[45] Aug. 2, 1977

[54] COMPOSITIONS CONTAINING ORGANO GERMANIUM COMPOUNDS USEFUL IN THE PREVENTION OF CARIES

[76] Inventors: Gerrit J. M. van der Kerk, Emmalaan 11; Antje Kaars Sijpesteijn, Hogendorpstraat 16, both of Utrecht; Eric J. Bulten, Julianalaan 149, Bilthoven, all of Netherlands

[21] Appl. No.: 584,117

[22] Filed: June 5, 1975

Related U.S. Application Data

[63] Continuation of Ser. No. 389,335, Aug. 17, 1973, abandoned.

[30] Foreign Application Priority Data

Aug. 21, 1972 Netherlands .................. 9211389

[51] Int. Cl.$^2$ .............................................. A61K 7/18
[52] U.S. Cl. ........................................ 424/52; 424/49; 424/56
[58] Field of Search .................................. 424/49–58

[56] References Cited

PUBLICATIONS

Sijpesteijn et al., Chem. Abst., 62, No. 2005A (1965) "Antimicrobial Activity of Trialkylgermanium Acetates and the Influence of the Medium", Abst. of Antonie Van Leeuwenhoek, J. Microbiol. Serol. 30(2):113–120 (1964).

Sijpesteijn et al., Chem. Abst. 60, No. 11309A (1964) "Antimicrobial Activity of Organogermanium Derivatives", Abst. of Nature 201 (4920):736 (1964) Chem. Abst., 58, No. 7308h (1963) of Antonie van Leeuwenhoek, J. Microbiol. Serol, 28:346–351 (1962) Antifungal and Antibacterial Activity of Some Trisubstituted Organogermanium, Organotin and Organolead Compounds".

Keyes et al., Chem. Abst., 79, No. 13921g (July 23, 1973) Abst. of J. Amer. Dent. Ass., 86(2):396–400 (1973) "Potential of Various Compounds to Suppress Micro-Organisms in Plaques Produced in Vitro by a Streptococcus or an Actinomycete".

Tanzer et al., Chem. Abst., 77, No. 70731c (Sept. 11, 1972) Abst. of Antimicrob. Agents Chemothor. 1(5):376–380 (1972) "Preclinical Evaluation of Antiplaque Agents".

*Primary Examiner*—Shep K. Rose
*Attorney, Agent, or Firm*—Lane, Aitken, Dunner & Ziems

[57] ABSTRACT

The addition of organo germanium compounds having the formula $$R_3GeX \text{ or } (R_3Ge)_2Y$$

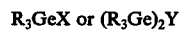

wherein R is an aliphatic or cycloaliphatic hydrocarbon group and X is an anion, such as carboxylate, sulphonate, halogen or hydroxyl, and Y is oxygen, sulphur, or sulphate, to conventional agents used in oral hygiene will significantly reduce the formation of plaque on teeth and thus reduce the incidence of caries. The preferred germanium compounds are the tri-n-butyl and tri-n-pentyl. The fluoride ion is the preferred anion because of its known anti-caries properties.

22 Claims, No Drawings

COMPOSITIONS CONTAINING ORGANO GERMANIUM COMPOUNDS USEFUL IN THE PREVENTION OF CARIES

This is a continuation of application Ser. No. 389,335 filed Aug. 17, 1973 now abandoned

BACKGROUND OF THE INVENTION

1. Field of the Invention

This invention relates to composition of matter useful in dental hygiene, more specifically in the prevention of caries.

2. Description of the Prior Art

One of the significant factors in the formation of caries is the conversion of soluble carbohydrates into acids. Inportant ingredients in this conversion process are the various types of lactic acid producing bacteria, including the genus *Streptococcus*. Accordingly, antibacterial substances have been added to toothpaste, rinses and other oral hygiene agents to control the growth and metabolism of oral bacteria and thereby eliminate or reduce the production of acids. The substances heretofore used to suppress bacterial growth have been characterized by a broad spectrum of activity which results in a marked change in the qualitative and quantitative composition of the microbial oral flora. These drastic changes are undersirable because many of the bacteria which are eliminated are beneficial for proper oral hygiene.

Recent studies (see, for instance, J. D. De Stoppelaar "*Streptococcus mutans, Streptococcus sanguis* and dental caries", dissertation Utrecht, 1st June 1971), have shown that although the production of acid from sugars, particularly by lactic acid bacteria, is a factor in the chain of caries formation, acid alone will not cause significant amounts of caries. These studies have established that the formation of "plaque", an insoluble, strongly adhering layer, is the primary factor in the causative chain. Acid producing bacteria and sugars which have been diffused into the plaque cause local acid production on or near the tooth surface. Animal tests have shown that such local production of acid is a direct cause of caries.

*Streptococcus mutans* (by its action on saccharose) has been identified as the only bacteria in the oral cavity which excretes the plaque forming, insoluble, high-molecular weight carbohydrate. Therefore, the suppression of the growth of *Streptococcus mutans* would significantly reduce caries formation by eliminating the formation of plaque.

A number of years ago a comparative study (A. Kaars Sijpesteijn et al., *On the Antifugal and Antibacterial Activity of Some Trisubstituted Organogermanium, Organotin and Organolead Compounds*, 28 Antonie van Leeuwenhoek 346 (1962) showed triorgano garmanium compounds, unlike the corresponding triorgano tin and lead compounds, have only slight antimicrobial effect. A few years later (A. Kaars Sijpesteijn et al., *Antimicrobial Activity of Trialkylgermanium Acetates and the Influence of the Medium*, 30 Antonie van Leeuwenhoek 113 (1964) it was found that some types of lactic acid bacteria displayed a high sensitivity to triorgano germanium compounds, particularly tributyl germanium compounds. For instance, *Streptococcus lactis* and *Streptococcus mitis* appeared to be very sensitive. However, *Streptococcus faecalis* was found to be entirely insensitive to tributyl germanium acetate. It was further observed that the activity of some tributyl germanium compounds is affected by the presence of slight amounts of blood or blood constituents in the nutrient medium. Thus some *Streptococcus* species, such as *Streptococcus lactis*, are ineffective in the presence of blood or blood constituents, while others, such as *Streptococcus mitis*, are not affected by their presences. From these and other studies neither the sensitivity nor insensitivity of certain Streptococcus species to triorgano germanium compounds nor the effect on the sensitivity of blood or blood constituents in the nutrient medium can be predicted rationally.

SUMMARY OF THE INVENTION

The object of this invention is to provide a composition which will retard formation of plague on the tooth surface and thereby reduce the incidence of caries.

More specifically, the object is to provide an additive for oral hygiene compositions which will retard the growth of *Streptococcus mutans*, thereby substantially reducing plague formation.

A further object is to retard the growth of *Streptococcus mutans* without substantially affecting the other bacteria present in the oral cavity.

These and other objects are accomplished by incorporating into an oral hygiene agent, such as toothpaste, rinses, mouthwashes tablets and the like, an organo germanium compound having the formula

$$R_3GeX \text{ or } (R_3Ge)_2Y$$

in which R is a branched or unbranched aliphatic or cycloaliphatic hydrocarbon group, X is an anion such as carboxylate, sulphonate, halogen or hydroxyl and Y is oxygen, sulphur or sulphate.

DETAILED DESCRIPTION OF THE INVENTION

The incorporation of the trialkyl germanium compounds described above into compositions used for oral hygiene provides a new and useful tool for combatting caries. The inventors have surprisingly found that *Streptococcus mutans* are very sensitive to trialkyl germanium compounds even in the presence of blood and blood constituents without substantially affecting the other bacteria present in the oral cavity.

Turing now to the specific organo germanium compounds of this invention disclosed above, R is an alkyl group preferably containing from 3 to 6 carbon atoms. The most preferred groups being n-butyl and n-pentyl because the germanium compounds having these substituents have the optimum activity against *Streptococcus mutans* and since the tri-n-alkyl germanium compounds display negligible toxicity in warm-blooded animals when administered either orally or intraperitoneally.

The nature of the anion, X, has little influence on the antimicrobial activity of the triorgano germanium compounds of this invention. Of course, in the case of the carboxylate and the sulphonate groups, the larger the number of carbon atoms on these radical the less antimicrobial obtained per unit of weight. The anion does have some effect on the physical properties of the compound and therefore the selection of the particular anion may be dependent on the nature of the composition into which the triorgano germanium compound is to be incorporated. The fluoride ion is a preferred anion because of its known effectiveness in fighting caries. In any event, the selection of a suitable anion for a particular use is well within the skill of the art.

As illustrated in the table below, even trace amounts, 3 ppm, will eliminate the visible growth of *Streptococcus mutans* in 2 days. However, it has been found that best results are obtained when the trialkyl germanium compound is incorporated into the oral hygiene composition in an amount from about 0.001 and 1 percent by weight, and preferably from about 0.01 and 0.5 percent by weight. It should be recognized that the upper limit is really a matter of economics since the organo germanium compounds have slight activity against microorganisms other than the *Streptococcus mutans* and have very low toxicity. On the other hand, the lower limits are really dependent upon the nature of the composition into which the germanium compound is incorporated. For these reasons, the concentration limits are stated as guidelines and not as limitations of the invention.

MINIMUM CONCENTRATION (μg/ml) WHICH CHECKS THE VISIBLE GROWTH COMPLETELY AFTER TWO DAYS AT 37° C

| Compound | Total Check (ppm) |
| --- | --- |
| tri-n-propyl germanium acetate | 30 |
| tri-iso-propyl germanium acetate | 30 |
| tri-n-butyl germanium acetate | 3 |
| tri-iso-butyl germanium acetate | 3 |
| tri-n-pentyl germanium acetate | 10 |
| tri-iso-pentyl germanium acetate | 3 |
| tri-n-hexyl germanium acetate | 100 |
| bis(tri-n-butyl)germanium oxyde | 3 |
| tri-n-butyl germanium fluoride | 3 |

The trialkyl germanium compounds of this invention may be incorporated into any oral hygiene agents. As used in this specification, the term "oral hygiene agent" includes any liquids, powders, pastes and tablets introduced into the oral cavity to aid in the prevention of caries and/or to affect the bacterial composition of the mouth and/or to effect the cleaning of teeth, in such a manner that the composition will coat the surface of substantially all the teeth in the oral cavity. By way of example, these agents include the heretofore enumerated toothpastes, mouthwashes, rinses and tablets (such as disclosing tablets) and professionally applied materials such as fluoride treatments and prophylaxis pastes. The types of agent into which the germanium compounds may be incorporated are in fact limited only by the nature in which the cleansing of the oral cavity is effected. It is essential that the agent contact substantially all of the tooth surfaces in the oral cavity because to prevent plague formation the germanium compound must retard the growth of *Streptococcus mutans* on these surfaces.

The oral hygiene agents containing the trialkyl germanium compounds of this invention are used in the same manner in which they are utilized in the absence of this additive. Obviously, if these agents are applied by the conventional techniques, the organo germanium compounds will contact substantially all of the tooth surfaces and thereby retard the growth of undersirable *Streptococcus mutans*.

The foregoing disclosure indicates that the incorporation of trialkyl germanium compounds in oral hygiene agents is a significant aid in combatting caries. This compound significantly checks the growth of *Streptococcus mutans*, the primary link in the series of cariogenic factors in the oral cavity, thus preventing the formation of plague, even in the presence of blood and blood constituents.

We claim:

1. A composition of matter useful in caries prevention comprising an oral hygiene agent, selected from fluoride treatments, powders, pastes or tablets, and an organo germanium compound which is effective to retard the growth of *Streptococcus mutans* and is selected from the group consisting of

$R_3GeX$ and $(R_3Ge)_2Y$ wherein
R is an aliphatic or cycloaliphatic hydrocarbon group,
X is a carboxylate group, a sulphonate group, a hydroxyl group or a halogen, and
Y is oxygen, sulphur or sulphate, the concentration of said compound in said oral hygiene agent being sufficient to retard the growth of *Streptococcus mutans* in the oral cavity.

2. The composition of matter as defined in claim 1 wherein R is an aliphatic or cycloaliphatic hydrocarbon group containing from 3 to 6 carbon atoms.

3. The composition of matter as defined in claim 2 wherein R is n-butyl or n-pentyl.

4. The composition of matter as defined in claim 1 wherein X is fluoride.

5. The composition of matter as defined in claim 1 wherein the concentration of said compound is at least about 0.001% by weight.

6. The composition of matter as defined in claim 5 wherein the concentration of said compound is from about 0.001% to about 1.0% by weight.

7. The composition of matter as defined in claim 6 wherein the concentration of said compound is from about 0.01% to about 0.5% by weight.

8. The composition of matter as defined in claim 1 wherein said oral hygiene agent is selected from toothpastes, disclosing tablets or prophylaxis pastes.

9. The composition as defined in claim 8 wherein the concentration of said compound is at least about 0.001% by weight.

10. The composition as defined in claim 9 wherein the concentration of said compound is from about 0.001% to about 1.0% by weight.

11. The composition as defined in claim 10 wherein the concentration of said compound is from about 0.01% to about 0.5% by weight.

12. The composition as defined in claim 9 wherein R is n-butyl or n-pentyl.

13. A composition of matter useful in caries prevention comprising an oral hygiene agent, selected from fluoride treatments, powders, pastes or tablets, and an organo germanium compound which is effective to retard the growth of *Streptococcus mutans* and is selected from the group consisting of

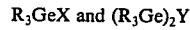

$R_3GeX$ and $(R_3Ge)_2Y$ wherein
R is an aliphatic or cycloaliphatic hydrocarbon group,
X is a carboxylate group, a hydroxyl group or a halogen, and
Y is oxygen or sulphur the concentration of said compound in said oral hygiene agent being sufficient to retard the growth of *Streptococcus mutans* in the oral cavity.

14. A composition of matter useful in dental hygiene comprising an oral hygiene agent, selected from fluoride treatments, powders, pastes or tablets, and an organo germanium compound which is effective to retard the growth of *Streptococcus mutans* and is selected from the group consisting of $$R_3GeX \text{ and } (R_3Ge)_2Y$$

wherein
R is an aliphatic or cycloaliphatic hydrocarbon group,
X is a carboxylate group, a sulphanate group, a hydroxyl group or a hologen, and
Y is oxygen, sulphur or sulphate,
the concentration of said compound in said oral hygiene agent being sufficient to retard the growth of *Streptococcus mutans* in the oral cavity.

15. A method of retarding the growth of *Streptococcus mutans* which comprises contacting *Streptococcus mutans* with an organo germanium compound selected from the group consisting of $R_3GeX$ and $(R_3Ge)_2Y$ wherein R is an aliphatic or cycloaliphatic hydrocarbon group, X is a carboxylate group, a sulphonate group, a hydroxyl group or a halogen, and Y is oxygen, sulphur or sulphate.

16. The method as defined in claim 15 wherein R is an aliphatic or cycloaliphatic hydrocarbon group containing from 3 to 6 carbon atoms.

17. The method as defined in claim 16 wherein R is n-butyl or n-pentyl.

18. The method as defined in claim 15 wherein X is fluoride.

19. A composition of matter useful in caries prevention comprising an oral hygiene agent, selected from fluoride treatments, powders, pastes or tablets, and an organo germanium compound selected from the group consisting of tri-n-propyl germanium acetate, tri-isopropyl germanium acetate, tri-n-butyl germanium acetate, tri-iso-butyl germanium acetate, tri-n-pentyl germanium acetate, tri-iso-pentyl germanium acetate, tri-n-hexyl germanium actate, bis(tri-n-butyl) germanium oxide and tri-n-butyl germanium fluoride, the concentration of said compound in said oral hygiene agent being sufficient to retard the growth of *Streptococcus mutans* in the oral cavity.

20. The composition of matter of claim 19 wherein said compound is bis(tri-n-butyl) germanium oxide.

21. A composition of matter comprising an oral hygiene composition, selection from fluoride treatments, powders, pastes or tablets, and an organo germanium compound which is effective to retard the growth of *Streptococcus mutans* and is selected from the group consisting of $$R_3GeX \text{ and } (R_3Ge)_2Y$$

wherein
R is an aliphatic or cycloaliphatic hydrocarbon group containing 3 to 6 carbon atoms,
X is acetate or fluoride, and
Y is oxygen or sulphur,
the concentration of said compound is said oral hygiene agent being sufficient to retard the growth of *Streptococcus mutans* in the oral cavity.

22. A composition of matter which will retard the growth of *Streptococcus mutans*, thereby substantially reducing plaque formation, comprising an oral hygiene agent, selected from fluoride treatments, powders, pastes or tablets, and an organo germanium compound which is effective to retard the growth of *Streptococcus mutans* and is selected from the group consisting of $$R_3ReX \text{ and } (R_3Ge)_2Y$$

wherein
R is an aliphatic or cycloaliphatic hydrocarbon group,
X is a carboxylate group, a sulphonate group, a hydroxyl group or a halogen, and
Y is oxygen, sulphur or sulphate,
the concentration of said compound in said oral hygiene agent being sufficient to retard the growth of *Streptococcus mutans* in the oral cavity.

* * * * *